United States Patent [19]

Tsukamoto et al.

[11] Patent Number: 4,564,593
[45] Date of Patent: Jan. 14, 1986

[54] MESSENGER RNA, PRODUCTION AND USE THEREOF

[75] Inventors: Kyozo Tsukamoto, Toyonaka; Shuji Hinuma, Suita; Haruo Onda, Kawanishi, all of Japan

[73] Assignee: Takeda Chemical Industries, Ltd., Osaka, Japan

[21] Appl. No.: 452,282

[22] Filed: Dec. 22, 1982

[30] Foreign Application Priority Data

Dec. 28, 1981 [JP] Japan .............................. 56-215723

[51] Int. Cl.[4] ..................... C12P 19/34; C07H 17/00; C12N 15/00; C12N 5/00
[52] U.S. Cl. ........................................ 435/91; 536/27; 435/70; 435/172.3; 435/240; 435/317; 935/1; 935/2; 935/3; 935/4; 935/16; 935/21
[58] Field of Search ................... 536/27; 435/68, 240, 435/172, 948, 172.3; 935/4, 16, 21, 53, 101

[56] References Cited

U.S. PATENT DOCUMENTS

| | | | |
|---|---|---|---|
| 4,260,737 | 4/1981 | Scherberg | 536/28 |
| 4,390,623 | 6/1983 | Fabricius et al. | 435/68 |
| 4,394,443 | 7/1983 | Weissmann et al. | 435/68 |
| 4,401,756 | 8/1983 | Gillis | 435/68 |
| 4,407,945 | 10/1983 | Gillis | 435/948 |
| 4,438,032 | 3/1984 | Golde et al. | 435/240 |

FOREIGN PATENT DOCUMENTS

| | | | |
|---|---|---|---|
| 0063482 | 10/1982 | European Pat. Off. | 935/4 |
| WO81/03498 | 12/1981 | PCT Int'L Appl. | 935/4 |

OTHER PUBLICATIONS

Efrat, S. et al, *Nature*, vol. 297, pp. 236–239, (1982), "Kinetics of Induction and Molecular Size of mRNA's encoding human–interleukin–2 and 8–interferon".
Maeda, S. et al, *Biochem. Biophysic. Res. Comm.* vol. 115, No. 3 (1983) pp. 1040–1047, "Cloning of Interleukin 2 mRNA's from Human Tonsils".
Mita, S. et al, *Biochem. Biophysic. Res. Comm.*, vol. 117, No. 1 (1983) pp. 114–121, "Isolation and Characterization of a Human Interleukin 2 Gene".
*Chemical Abstracts*, vol. 91, 1979, p. 293, abstract No. 153801 r: Colman, A. et al, "Export of Proteins from Oocytes of *Xehopus Laevus*". Carrying this Gene, a Living Cell Line Possessing the Recombinant DNA, and a Method for Producing Interleukin–2 Using this Cell".
Maniatis, T. et al, *Molecular Cloning: A Laboratory Manual,* Cold Spring Harbor Laboratory, New York (1982), pp. 344–352.
*The Merck Index,* 10th Edition, Windholz, M. et al, editors, Merck and Co. Inc., Rahway, N.J. p. 1057 (1983).
*Methods in Enzymology,* vol. XXX, part F, Nucleic Acids and Protein Synthesis, pp. 605–631, Academic Press, New York, Moldave, K. et al, editors (1974)
*Chemical Abstracts,* vol. 100, 1984, p. 144, abstract No. 62754r: Degrave, W. et al, "Cloning and Structure of the Human Interleukin 2 Chromosomal gene".
*Chemical Abstracts,* vol. 100, 1984, p. 454, abstract No. 66412a: Bettens, F. et al, "Lymphokine regulation of Activated ($G_1$) lymphocytes. II. Glucocorticoid and Anti-Tac-Induced Inhibition of Human T Lymphocyte Proliferation".
*Chemical Abstracts,* vol. 100, 1984, p. 166, abstract No. 97628e: Taniguchi, T. et al, "Gene Coding for Interleukin–2 polypeptide, Recombinant DNA.
Immunological Review, 51, 257–278 (1980).
Science, 193, 1007–1008 (1976).
Journal of Immunology, 123, 2928–2929 (1979).
Nature, 268, 154–156 (1977).
Nature, 280, 685–688 (1979).

(List continued on next page.)

*Primary Examiner*—Thomas G. Wiseman
*Assistant Examiner*—Joanne M. Giesser
*Attorney, Agent, or Firm*—David G. Conlin

[57] ABSTRACT

The present invention provides human Interleukin 2-encording messenger RNA which is free of human cells, a method of producing the same from the cells which are capable of producing human Interleukin 2 and a method of producing human Interleukin 2 using the same in an in vitro protein synthesis system.

6 Claims, 1 Drawing Figure

OTHER PUBLICATIONS

Journal of Immunology, 125, 1904–1909 (1980).
Journal of Immunology, 126, 1120–1125 (1981).
Journal of Immunology, 126, 2321–2327 (1981).
European Journal of Immunology, 10, 719–722 (1980).
Nature, 284, 278–280 (1980).
Scandinavian Journal of Clinical and Laboratory Investigations, supplement to vol. 21, 97, 77 (1968).
Journal of American Medical Association, 199, 519–524 (1967).
Biochemical Journal, 183, 181–184 (1979).
Biochemistry, 18, 5143–5149 (1979).
Proceedings of National Academy of Sciences, U.S.A., 77, 6134–6138 (1980).
Blood, 57, 379–394 (1981).
Nature, 233, 177–182 (1971).
Journal of Experimental Medicine, 152, 1709–1719 (1980).
Journal of Immunology, 127:2432–2435 (1981).
Journal of Immunology, 110:546–557 (1973).

MESSENGER RNA, PRODUCTION AND USE THEREOF

This invention relates to a messenger RNA coding for human Interleukin 2.

More particularly, this invention provides a novel, human Interleukin 2-encoding messenger RNA, a method of producing the same and a method of producing human Interleukin 2 using the same.

Human Interleukin 2 is a factor essential for the proliferation of human T cells [Immunological Review, 51, 257 (1980)]. Thus, it is an essential factor in growing and maintaining human T cells, which take the leading role in various immune reactions, by continuous culture in vitro without altering the functions thereof. A factor capable of promoting the growth of T cells was found in the supernatant from a culture of lectin-stimulated human peripheral blood lymphocytes and named TCGF (T-cell growth factor), [Science, 193, 1007 (1976)]. Later, it was suggested that this TCGF activity-showing factor should be identical with the thymocyte mitogenic factor or with the factor capable of enhancing the antibody production in nude mice, and these lymphokines were collectively named Interleukin 2 (hereinafter some times abbreviated to "IL-2") [Journal of Immunology, 123, 2928 (1979)]. Whereas the specific structure of each of these factors is not so clear for the time being, the possibility that one and the same factor is called by different names as a result of their having been studied by different assay methods is high. Discovery of IL-2 has enabled long-term culture of normal T cells with their functions being maintained and as a result, out of T cells, killer T cells or natural killer cells or, in some cases, helper T cells have been cloned (e.g. Nature, 268, 154 (1977)]. In addition to these direct applications, i.e. the use of IL-2 in in vitro subculture or cloning of normal T cells, IL-2 has other applications such as mentioned below. Thus, the use of IL-2 can lead to in vitro proliferation of antigen-specific killer T cells which can recognize and destruct cells having specific antigens, e.g. tumor antigens (Nature, 280, 685 (1979)]. In fact, it is known that, in animal experiments, killer T cells proliferated in this manner, when returned to the animals, can inhibit tumor growth [Journal of Immunology, 125, 1904 (1980)]. Furthermore, it is also known, for instance, that the addition of IL-2 to a lymphocyte culture system induces the production of interferon γ [Journal of Immunology, 126, 1120 (1981)] or causes activation of natural killer cells [Journal of Immunology, 126, 2321 (1981)]. These facts suggest further the possible utility of IL-2 as an antitumor agent. It is further known that IL-2 can restore the helper T cell function in nude mice which are said to be deficient in thymus functions [European Journal of Immunology, 10, 719 (1980)] or can restore the induction of killer T cells against allogeneic tumor cells [Nature, 284, 278 (1980)], and the use of IL-2 in diseases resulting from decreased or deficient immune functions can be expected to be fruitful.

However, it is very difficult to collect human IL-2, whose utility can thus be expected in a variety of fields, from living human bodies because it is present in the organisms in extremely small amounts. At present, the inducer (e.g. lectin)-treated human lymphocyte culture supernatant is used for the preparation of human IL-2. However, the supply of lymphocyte materials such as human blood is limited and moreover the production from such culture is very small as is usual with lymphokines in general. Accordingly, development of a production method which can supply large amounts of purified IL-2 has strongly been desired.

For obtaining human IL-2 in large amounts, it is at first conceivable to use the so-called gene manipulation technique. However, so far no information was available on the human IL-2-encoding messenger RNA, which is the basic element for realizing said technique, and not only the structure but also properties thereof were unknown. There was no clue at all.

The present inventors have now succeeded in isolating for the first time a messenger RNA coding for human IL-2 from human cells and have established a method of producing human IL-2 by introducing said messenger RNA into an in vitro protein synthesis system, incubating said system for formation and accumulation of human IL-2 and recovering the same.

As the cells from which said messenger RNA is to be isolated, there may be used any cells that are capable of producing human IL-2. Preferred are human lymphocytic cells and leukocytic cells, among others, because relatively large amounts can be recovered with them. The use of peripheral blood-derived lymphocytes is especially advantageous.

Said cells can be isolated, for instance, from the peripheral blood by applying, for example, the method using dextran [Journal of Immunology, 110, 546 (1973)] or the specific gravity centrifugation method using Ficoll-Hypaque [Scandinavian Journal of Clinical and Laboratory Investigations, supplement to vol. 21, 97, 77 (1968)].

The human IL-2-encoding messenger RNA according to the invention can be produced by growing cells capable of producing human IL-2 in the presence of an inducer so as to cause formation and accumulation of the human IL-2-encoding messenger RNA in said cells and isolating or collecting the same.

The medium to be used in growing human IL-2-producing cells may be of any type provided that said cells can accumulate human IL-2 in the medium. Nevertheless, media for animal cell culture are suited for the cultivation purpose. Thus, for example, a commercially available medium RPMI-1640 [Journal of American Medical Association, 199, 519 (1967)] can advantageously be used. It is preferable to add an animal serum, antibiotic and so on. Fetal calf serum or calf serum is preferable as the animal serum and it is added generally in an amount of 0.1 to 50 percent, preferably 2 to 20 percent (on the medium basis). The antibiotic includes, among others, kanamycin, penicillin and streptomycin and is added generally to a concentration of 0.05 to 1 mg/ml.

The inducer to be used includes substances capable of inducing formation of IL-2, such as Lectins [e.g. concanavalin A (ConA), phytohemagglutinin (PHA)] and/or various antigens and phorbol esters [e.g. 12-0-tetradecanoylphorbol 13-acetate (TPA)]. Although these may be used singly, combined use thereof can induce IL-2 efficiently. The lectin-phorbol ester combination is preferable. More particularly, when ConA, for instance, is used as the lectin and TPA, for instance, is used as the phorbol ester, they are added in concentrations of 5 to 80 μg/ml and 1 to 50 ng/ml, respectively.

The incubation is performed in the manner of static culture, spinner culture and so on. Spinner culture is preferable for large-scale production. Inoculation is generally conducted in a cell concentration of 0.1 to $50 \times 10^6$ cells/ml, preferably 1 to $5 \times 10^6$ cells/ml, and incubation is conducted at 30° to 40° C.

The incubation period is selected, for example, on the basis of induction and production of IL-2 itself. Generally, the formation and accumulation of the desired messenger RNA reaches a maximum normally in about 5 to 80 hours, which is about half the time in which production of IL-2 attains its maximum especially about 20 to 40 hours, and it is preferable to separate and recover said messenger RNA from the cells at that point of time.

The RNA fraction containing the messenger RNA of the invention can generally be separated from the cells by lysing the cells by a chemical or physical means and then applying a per se known extraction method [method of Kaplan et al.: Biochemical Journal, 183, 181 (1979); method of Berger et al.: Biochemistry, 18, 5143 (1979)].

Thus, for example, the above-mentioned cultured cells are harvested by centrifugation and, following addition of 2 to 10 volumes (based on the harvested cells) of a buffer solution containing a thiocyanate (e.g. guanidine thiocyanate) and a mercaptoalkanol (e.g. 2-mercaptoethanol), they are triturated. The thus-obtained homogenate, preferably with cesium chloride, for instance, added thereto, is layered on cesium chloride in a centrifugal tube or the like and centrifuged at 15,000 to 30,000 revolutions per minute for 10 to 30 hours for RNA sedimentation. The supernatant is removed, the RNA precipitate is dissolved in a buffer, sodium chloride and further a lower alkanol (e.g. ethanol) are added thereto, and RNA precipitation is caused under cooling (0° C. to −40° C.). There is obtained an RNA fraction by the above extraction procedure.

The desired messenger RNA can be isolated from the thus-obtained mixture of various RNAs by an appropriate combination of techniques selected from among sucrose density gradient centrifugation, gel filtration, electrophoresis, membrane filter method, oligo(dT) column method and so on. In a preferred embodiment, fractionation by oligo(dT)-cellulose column chromatography is followed by sucrose density gradient centrifugation to get said messenger RNA.

Thus for example, the alkanol-precipitated RNA fraction is collected by centrifugation, dissolved in a buffer, adsorbed on an oligo(dT) column and eluted with an SDS(sodium dodecyl sulfate)-containing buffer. The thus-obtained polyadenylic acid-bound RNA is dissolved in an SDS-containing buffer, the solution is layered on density gradient solutions generally containing 10-30% sucrose, fractionation is performed by centrifugation, and there can be obtained the messenger RNA of the present invention.

The thus-obtained messenger RNA, free of human cell, coding for human IL-2 of the present invention has the following properties: (1) a sedimentation coefficient of 8S to 15S (2) polyadenylic acid structure at its 5' terminus and (3) it codes for a human IL-2.

In producing human IL-2 using the messenger RNA of the invention, 10 to 500 ng/cell of the RNA, preferably after dissolution in a buffer, is introduced into an in vitro protein synthesis system by a known method and incubation is performed at 20° C. to 40° C. generally for 1 to 48 hours. As the in vitro protein synthesis system, there may be used any system in which IL-2 can be produced by introduction of the messenger RNA prepared in accordance with the invention, such as a protein synthesis system comprising or derived from *Xenopus laevis* oocytes, rabbit reticulocytes, wheat germs or cultured mammalian cells. *Xenopus laevis* oocytes are favorable because of high productivity.

The activity of the IL-2 thus produced can be measured by any known method of assaying IL-2 species, such as TCGF, co-stimulating factor (CoS), T-cell replacing factor, thymocyte stimulating factor, killer helper factor and thymocyte mitogenic factor [Immunological Review, 51, 257 (1980)]. However, it is desirable to perform the assay method for TCGF activity, which is the method of assaying the most typical IL-2 activity, namely T cell proliferation-promoting activity. Furthermore, it is more desirable to additionally conduct an assay for at least one kind of IL-2 activity other than the TCGF activity, for example CoS activity. Since it is known that the human TCGF is effective not only against human cells but also against mouse cells, TCGF-dependent mouse cells can be used in the assay for human TCGF in addition to TCGF-dependent human cells [Immunological Review, 51, 257 (1980)].

Human IL-2 can be produced, as mentioned above, by introducing the messenger RNA coding for human IL-2 into an appropriate protein synthesis system. Furthermore, the whole structural gene (DNA) coding for IL-2 will be synthesized from said messenger RNA in vitro using a reverse transcriptase, cloned, inserted into, for example, an appropriate plasmid DNA and introduced into an appropriate host, for example *Escherichia coli*; cultivation of the host will produce highly pure human IL-2 in large amounts. In this case, since the starting material is a messenger RNA, the gene does not contain any introns that are found in higher animal genome. This means that the structural gene for IL-2 can be transcribed in bacterial cells and expressed as the IL-2-encoding messenger RNA. Therefore, it will be possible to produce inexpensive human IL-2 in large amounts when this IL-2 gene is bound to an appropriate regulatory gene, inserted into a plasmid DNA and introduced into bacterial cells.

Human IL-2 is a relatively stable protein having a molecular weight of about 12,000 to 13,000. It has no sugar chain [Proceedings of National Academy of Sciences, USA, 77, 6134 (1980)] or if it has, the sugar chain appears to have little effect on its activity itself [Blood, 57, 379 (1981)]. It thus satisfies the conditions required for the production thereof as a protein by a recombinant DNA technique.

Figure 1:
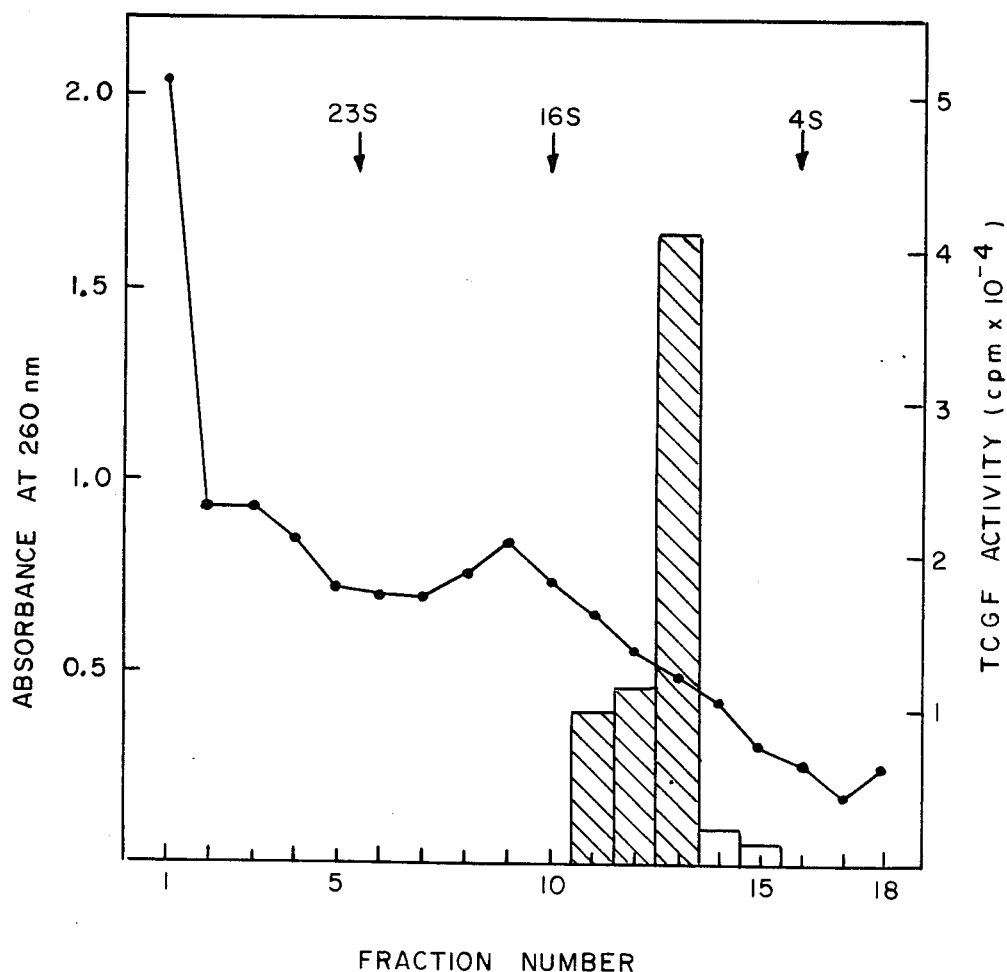
FIG. 1 shows the TCGF activity data for the IL-2 obtained in Example 3—(3).

In the figure,

▲: absorbance at 260 nm;

▨: TCGF activity.

The following examples illustrate the invention in more detail.

EXAMPLE 1

Induction and isolation of human IL-2-encoding messenger RNA (1) Preparation and cultivation of human peripheral blood lymphocytes and induction of human IL-2

The buffy coat (the pale yellow leukocyte layer found on the lower erythrocyte layer when blood is centrifuged) cells collected from a blood material taken from 10–15 healthy humans (about 300 ml per capita) were used as the starting material. After the blood collection, the buffy coat cells were stored at 4° C. overnight and then mixed with an equal volume of RPMI-1640 medium (Micro Biological Associates USA), and a half volume of physiological saline containing 3% dextran (Meito Sangyo Ltd., Japan; molecular weight 300,000-500,000) was then added. The mixture was allowed to stand at room temperature for 30-40 minutes. The supernatant was collected and centrifuged at 2,000 revolutions per minute (rpm) for 5 minutes and, following re-addition of RPMI-1640 medium to the cells collected by centrifugation, centrifugation was repeated. (In this manner, the cells were washed twice.) RPMI-1640 medium containing 10% fetal calf serum (F.C.S.) and antibiotics (100 units/ml of penicillin and 100 μg/ml of streptomycin) was added to the cells collected by centrifugation to a cell concentration of $5 \times 10^6$ cells/ml. The cell-containing medium was transferred to a spinner flask (1-3 liters) and incubated at 37° C. with stirring at a rate of 50 rpm. Then, 15 ng/ml of TPA was added. After incubation for 3 hours, 40 μg/ml of ConA (PL Ltd. USA) was further added to the above incubation system, and incubation was continued for further 24 hours to induce IL-2.

(2) RNA extraction from lymphocytes subjected to IL-2 induction

The method of Kaplan et al. [Biochemical Journal, 183, 181 (1979)] was mainly used for whole RNA extraction from lymphocytes following IL-2 induction. Thus, 24-48 hours after IL-2 induction, cells were collected by centrifugation at 2,000 rpm for 10 minutes, 5 volumes (based on the cell volume) of a solution composed of 5M guanidine thiocyanate, 0.01M Tris-HCl pH 7.6 and 6.5% of 2-mercaptoethanol was added and the cells were triturated 15-20 times in a 200-ml Teflon homogenizer. To 1 ml of the thus-obtained homogenate, 0.5 g of cesium chloride was added, and the mixture was then layered on 7 ml of 5.7M cesium chloride solution in a centrifugal tube for a Spinco SW27 rotor. Centrifugation was conducted at 24,000 rpm for 20 hours for RNA precipitation. The supernatant in the tube was removed by suction, the upper portion of the tube was cut off to leave about 2 cm from the bottom, and the RNA precipitate was dissolved in 0.01M Tris-HCl buffer (pH 7.6) containing 0.4% of N-lauroylsarcosine, 2 mg/ml of heparin and 0.2% of diethyl pyrocarbonate. To this solution were added sodium chloride and cold ethanol to final concentrations of 0.2M and 70%, respectively, and the resultant mixture was allowed to stand at $-20°$ C. for RNA precipitation.

(3) Preparation of polyadenylic acid-bound RNA by oligo(dT)-cellulose column chromatography The ethanol-precipitated RNA was collected by centrifugation in a Spinco SW27.1 rotor at 20,000 rpm for 20 minutes, and dissolved in 10 ml of Tris-HCl buffer (pH 7.6) containing 0.5M NaCl, 0.0001M EDTA and 0.5% of SDS. Oligo(dT)-cellulose (PL Ltd., U.S.A.) dissolved in the same buffer as above was placed in a 10-ml syringe to a height of 4 cm (4 ml). The above RNA specimen was passed through the column two times, whereby polyadenylic acid-bound RNA was absorbed thereon. The unadsorbed RNA species were washed with the same buffer until the ultraviolet absorption at 260 nm was no more detected. The polyadenylic acid-bound RNA was eluted from the column with 10 mM Tris-HCl buffer (pH 7.6) containing 0.001M EDTA and 0.3% of SDS (1 ml/fraction). Each fraction was then subjected to absorbance measurement at 260 nm. The RNA-containing fractions were combined and subjected to ethanol precipitation in the manner mentioned under (2) in Example 1.

(4) Fractionation by sucrose density gradient centrifugation

About 0.5-1 mg of the polyadenylic acid-bound RNA obtained by the above procedure was dissolved in 0.01M Tris-HCl buffer (pH 7.6) containing 0.05M sodium chloride, 0.01M EDTA and 0.2% of SDS and the solution was layered on 10-30% sucrose density gradient-constituting solutions. Centrifugation was performed in an SW27 rotor at 20° C. at 25,000 rpm for 21 hours. The contents were fractionated into 18 fractions. Based on the absorbance values measured at 260 nm, the 11S fraction and nearby fractions were respectively subjected to ethanol precipitation. The desired messenger RNA was thus obtained as a precipitate. As the standards for S-value determination, 23S, 16S and 4S *E. coli* RNAs (Miles Ltd. U.S.A.) were centrifuged in the same manner in separate centrifugal tubes.

The yield of the thus-obtained messenger RNA for IL-2 activity as contained in 8S to 15S fractions was 160 μg.

EXAMPLE 2

Production of human IL-2

A female individual of *Xenopus laevis*, 10 cm in body length, was anesthetized by immersing it in ice water and anatomized for taking out oocytes. Using a stainless steel wire, the oocytes were separated one by one in Barth's culture medium [Nature, 233, 177 (1971)]. The messenger RNA obtained by the procedure mentioned under (4) in Example 1 was dissolved in a buffer solution (88 mM sodium chloride, 1.0M potassium chloride, 15 mM Tris-HCl pH 7.6) in a concentration of 1 mg/ml. 100 nl (100 ng) portions of the solution were injected into the individual ooctyes using a capillary and a micromanipulator under a stereoscopic microscope. For each RNA sample, 20-30 ooctyes were used. They were incubated in 0.3 ml of Barth's medium at 24° C. for 24 hours. Then, the culture supernatant was centrifuged on a Servall centrifuge at 15,000 rpm for 30 minutes to give a supernatant. The fact that this supernatant contained human IL-2 was confirmed by the procedure mentioned under (3) in Example 3.

EXAMPLE 3

Assay of human IL-2

(1) Human IL-2 activity of the culture supernatant (effects of kind and concentration of lectin on IL-2 production and the change in IL-2 productivity with time)

The reaction between the IL-2 activity of the culture supernatant and the lectin concentration used for IL-2 induction is shown in Table 1. The human IL-2 activity was measured by using mouse TCGF-dependent cell line NKC3 [Proceedings of Japanese Society of Immunology, 11, 277 (1981)]. Thus, 50 μl each of samples diluted by two-step dilution and having varied concentrations was placed in a flat-bottomed microplate (Falcon Ltd. U.S.A.). Then, 50 μl of RPMI-1640 medium containing $3 \times 10^4$ NKC3 cells and 10% fetal calf serum (10% FCS) was added and incubation was performed in a carbon dioxide incubator at 37° C. for 20 hours. $^3$H-thymidine (1 μCi) was added and incubation was further conducted for 4 hours. Using a cell harvester (Waken Yaku Kogyo Ltd., Japan), the cells were trapped on a glass filter, washed, filtered, dried and subjected to radioactivity determination with a scintillation counter. The intensity of the activity of a sample was expressed as a relative value (in units/ml) based on the intensity of the activity of a standard sample as obtained in the following manner. Thus, a certain culture supernatant prepared in the same manner as in Example 1—(1) but collected 120 hours after induction was used as the standard sample and it was assumed that the activity thereof was equal to 1 unit/ml. First, the sample to be assayed and the standard sample were diluted in several steps and the values for $^3$H-thymidine intake as obtained for each sample were plotted on a Probit paper, whereby a linear relationship was obtained between the sample concentration and the $^3$H-thymidine intake. The degree of dilution, or concentration, at which, when the maximum intake was regarded as 100% intake, 50% intake was attained was read from the diagram obtained. This concentration was divided by the concentration of the standard sample which gave 50% intake, to give the activity in units/ml of the test sample. FIG. 1 shows the TCGF activity data in units/ml as calculated in the above manner for culture supernatants 48 hours after induction using 15 ng/ml of TPA plus varied concentrations of ConA or 15 ng/ml of TPA plus varied concentrations of PHA as inducers in the procedure of Example 1—(1).

TABLE 1

Effect of Con A and PHA on TCGF production

| Lectin | Concentration | TCGF activity (units/ml) |
|---|---|---|
| Con A | 0 (μg/ml) | <0.01 |
|  | 2.5 | 0.01 |
|  | 5 | 0.35 |
|  | 10 | 1.30 |
|  | 20 | 4.0 |
|  | 40 | 6.5 |
|  | 80 | 3.0 |
| PHA | 0 (%) | <0.01 |
|  | 0.0625 | 4.0 |
|  | 0.125 | 5.3 |
|  | 0.25 | 4.6 |
|  | 0.5 | 4.9 |
|  | 1 | 3.5 |
|  | 2 | 4.0 |

Table 2 shows the change with time in TCGF production when 40 μg/ml of ConA and 15 ng/ml of TPA, or 0.5% of PHA and 15 ng/ml of TPA were used in the procedure of Example 1—(1).

TABLE 2

The change with time in TCGF production using Con A or PHA

| Lectin | Hours | TCGF activity (units/ml) |
|---|---|---|
| Con A | 24 | 1.2 |
|  | 48 | 2.1 |
|  | 72 | 2.6 |
|  | 120 | 2.0 |
| PHA | 24 | 0.3 |
|  | 48 | 1.5 |
|  | 72 | 2.5 |
|  | 120 | 2.0 |

As shown in Table 1 and Table 2, it has become clear that ConA in a concentration of about 40 μg/ml and PHA in a concentration of 0.125% or above can cause production of almost the same, highest level of TCGF activity and that, in each case, the culture supernatant TCGF activity reaches the highest value in 72 hours after induction.

(2) Production of human IL-2 (TCGF and CoS) using the oligo(dT) column-fractionated messenger RNA for human IL-2

The procedure of Example 1—(1) was followed using 0.5% of PHA and 15 ng/ml of TPA as the inducers, and RNA extraction was carried out 24 hours after induction by the procedure of Example 1—(2). The RNA obtained was subjected to oligo (dT) column treatment by the procedure of Example 1—(3), and the thus-obtained, human IL-2-encoding messenger RNA fraction was injected into oocytes of *Xenopus laevis* by the procedure of Example 2 and the oocytes were incubated. The IL-2 activity of the culture supernatant obtained by centrifugation was measured in terms of TCGF activity mentioned in Example 3—(1) and in terms of CoS activity as an example of other activity-expressing forms than the TCGF activity. The CoS activity measurement was conducted in the following manner. Thymus cells ($2.5 \times 10^5$ cells) of a BALB/C mouse (8-10 weeks of age) were suspended, together with 5 μg/ml of ConA and an adequately diluted sample, in 100 μl of RPMI-1640 solution containing 10% FCS, $1 \times 10^{-5}$M mercaptoethanol and antibiotics, and the suspension was incubated in a flat-bottomed microplate for 72 hours. Four hours prior to the end of incubation, 1 μCi of $^3$H-thymidine was added, and the intake into the cell was measured using a cell harvester in the same manner as in the case of TCGF activity measurement. The intensity of the activity was expressed as the $^3$H-thymidine intake-enhancing effect, namely as the difference from the uptake value for the control group in which no sample was added. In Table 3, there are shown the TCGF activity data (expressed directly as $^3$H-thymidine intake values, not in units/ml, for easy comparison with the CoS activity data) and CoS activity data for the centrifugation supernatant of the messenger RNA-injected *Xenopus laevis* oocyte culture.

TABLE 3

Production of TCGF and CoS by the messenger RNA coding for human IL-2 (oligo(dT) column fraction)

| Dilution of sample | TCGF activity (cpm) | | CoS activity (cpm) | |
|---|---|---|---|---|
|  | mRNA injection | saline injection | mRNA injection | saline injection |
| $2^2$ | 5,005(±60) | 420(±0) | 7,709(±1685) | 580(±160) |
| $2^3$ | 3,733(±158) | 413(±63) | 4,978(±572) | 695(±150) |
| $2^4$ | 2,285(±55) | 400(±25) | 2,037(±137) | 865(±200) |
| $2^5$ | 1,330(±65) | 520(±70) | 1,655(±200) | 623(±33) |
| $2^6$ | 918(±53) | 495(±155) | 1,370(±170) | 743(±88) |
| $2^7$ | 720(±35) | 520(±20) | 1,100(±195) | 835(±70) |

Each value represents the mean of two measurements.

As shown in Table 3, it is evident that IL-2 detectable not only as TCGF activity but also as CoS activity can be produced by injecting into *Xenopus laevis* oocytyes the polyadenylic acid structure-containing messenger RNA fractionated by the oligo(dT) column.

(3) Production of IL-2 using the human IL-2-encoding messenger RNA obtained by sucrose density gradient centrifugation.

Induction was carried out using 40 μg/ml of ConA and 15 ng/ml of TPA and following the procedure of Example 1. RNA extraction was performed 24 hours later. 50 μl of the supernatant prepared by the procedure of Example 2 was two-fold diluted and then assayed for TCGF activity by the method mentioned in Example 3—(1). The results obtained are shown in FIG. 1. The TCGF activity was expressed in terms of the $^3$H-thymidine uptake value. As can be seen from the figure, fraction No. 13 showed a peak in IL-2-encoding messenger RNA content and the fractions corresponding to 8S to 15S as judged on the basis of the fractionation pattern obtained with the standard RNAs for S value determination revealed the activity of directing the synthesis of IL-2.

The following references, which are referred to for their disclosures at various points in this application, are incorporation herein by reference.

Immunological Review, 51, 257 (1980)
Science, 193, 1007 (1976)
Journal of Immunology, 123, 2928 (1979)
Nature, 268, 154 (1977)
Nature, 280, 685 (1979)
Journal of Immunology, 125, 1904 (1980)
Journal of Immunology, 126, 1120 (1981)
Journal of Immunology, 126, 2321 (1981)
European Journal of Immunology, 10, 719 (1980)
Nature, 284, 278 (1980)
Scandinavian Journal of Clinical and Laboratory Investigations, supplement to vol. 21, 97, 77 (1968)
Journal of American Medical Association, 199, 519 (1967)
Biochemical Journal, 183, 181 (1979)
Biochemistry, 18, 5143 (1979)
Proceedings of National Academy of Sciences, U.S.A., 77, 6134 (1980)
Blood, 57, 379 (1981)
Nature, 233, 177 (1971)
Proceedings of Japanese Society of Immunology, 11, 277 (1981)

What is claimed is:

1. A culture of cells containing exogenous messenger RNA isolated from human cells which has a sedimentation coefficient of 8S to 15S and which codes for human Interleukin 2.

2. Substantially pure messenger RNA isolated from human cells, which has a sedimentation coefficient of 8S to 15S and which codes for human Interleukin 2.

3. Substantially pure messenger RNA according to claim 1, wherein the human Interleukin 2 is human T-cell growth factor or human co-stimulating factor.

4. A method of producing messenger RNA isolated from human cells, the messenger RNA having a sedimentation coefficient of 8S to 15S and coding for human Interleukin 2, which comprises growing human Interleukin 2-producing lymphocytic cells isolated from human peripheral blood, in a medium for animal cell culture containing lectin and phorbol ester as an inducer, at 30° to 40° C., by spinner culture, for about 5 to 80 hours, to cause formation and accumulation of the messenger RNA in the cells, harvesting the grown cells by centrifugation, homogenizing the resulting cells in the presence of buffer containing thiocyanate and mercapto-alkanol, centrifuging the homogenate in the presence of cesium chloride, precipitating RNA from the resulting supernatant by adding sodium chloride and lower alkanol, and purifying the RNA by oligo (dT)-cellulose column chromatography and sucrose density gradient centrifugation.

5. A method according to claim 3, wherein the inducer comprises concanavalin A as lectin and 12-O-tetradecanoylphorbol 13-acetate as phorbol ester in the concentrations between about 5 to 80 μg/ml and 1 to 50 ng/ml, respectively.

6. The process of producing cDNA coding for human Interleukin 2 comprising contacting messenger RNA isolated from human cells and coding for human Interleukin 2 with reverse transcriptase for a time and under conditions sufficient to form said cDNA.

* * * * *

UNITED STATES PATENT AND TRADEMARK OFFICE
CERTIFICATE OF CORRECTION

PATENT NO. : 4,564,593

DATED : January 14, 1986

INVENTOR(S) : Tsukamoto et al.

It is certified that error appears in the above—identified patent and that said Letters Patent is hereby corrected as shown below:

Claim 1, line 3, delete "85", insert--8S--.
Claim 1, line 3, delete "155", insert--15S--.
Claim 3, line 2, delete "1", insert--2--.
Claim 5, line 1, delete "3", insert--4--.

Signed and Sealed this

Twelfth Day of August 1986

[SEAL]

Attest:

Attesting Officer

DONALD J. QUIGG

Commissioner of Patents and Trademarks